(12) United States Patent
Sakovich et al.

(10) Patent No.: US 7,824,524 B2
(45) Date of Patent: Nov. 2, 2010

(54) HIGHLY PROTONATED, SUPERCHARGED, LOW PH, NON-CORROSIVE COMPOSITION

(75) Inventors: Anthony P. Sakovich, New Port Richey, FL (US); Burt R. Sookram, Palm Harbor, FL (US)

(73) Assignee: S & B Worldwide Corporation, Palm Harbor, FL (US)

( * ) Notice: Subject to any disclaimer, the term of this patent is extended or adjusted under 35 U.S.C. 154(b) by 0 days.

(21) Appl. No.: 12/511,092

(22) Filed: Jul. 29, 2009

(65) Prior Publication Data

US 2010/0006418 A1 Jan. 14, 2010

Related U.S. Application Data

(62) Division of application No. 12/171,382, filed on Jul. 11, 2008.

(51) Int. Cl.
| | |
|---|---|
| C01B 17/00 | (2006.01) |
| C11D 3/02 | (2006.01) |
| C11D 7/02 | (2006.01) |
| C11D 3/20 | (2006.01) |
| C11D 1/22 | (2006.01) |
| A01K 43/00 | (2006.01) |
| A61K 8/00 | (2006.01) |
| A61Q 1/14 | (2006.01) |
| A61Q 19/00 | (2006.01) |
| A61Q 19/10 | (2006.01) |
| C07C 323/25 | (2006.01) |
| A01N 59/02 | (2006.01) |
| A61K 33/04 | (2006.01) |

(52) U.S. Cl. .................. 204/157.49; 510/492; 510/495; 510/111; 510/130; 510/508; 424/703; 424/709; 424/710; 424/713

(58) Field of Classification Search ................. 510/508, 510/492, 495, 111, 130; 424/710, 703, 709, 424/713; 514/588, 886, 887; 422/29, 905; 252/183.11–183.16; 204/157.49
See application file for complete search history.

(56) References Cited

U.S. PATENT DOCUMENTS

| | | |
|---|---|---|
| 4,010,240 A | 3/1977 | von Plessen et al. |
| 5,989,595 A | 11/1999 | Cummins |
| 6,242,011 B1 | 6/2001 | Cummins |
| 6,565,893 B1 | 5/2003 | Jones et al. |
| 7,192,618 B2 | 3/2007 | Cummins et al. |
| 2003/0050199 A1 | 3/2003 | Kemp et al. |
| 2005/0191365 A1* | 9/2005 | Creasey et al. ............... 424/618 |
| 2007/0190175 A1 | 8/2007 | Cummins et al. |

* cited by examiner

*Primary Examiner*—Lorna M Douyon
*Assistant Examiner*—Tanisha Diggs
(74) *Attorney, Agent, or Firm*—Dennis G. LaPointe

(57) ABSTRACT

A highly protonated, supercharged, low pH, non-corrosive composition and process for making the composition wherein the composition has a milli-volt charge between 400 and 1400, a proton count between $8 \times 10^{\wedge} \geqq$ and $14 \times 10^{\wedge} \geqq$, and a pH level at 1 part composition with 99 parts water between 0.9 and 1.8.

3 Claims, No Drawings

HIGHLY PROTONATED, SUPERCHARGED, LOW PH, NON-CORROSIVE COMPOSITION

RELATED APPLICATION

This application is a divisional of U.S. patent application Ser. No. 12/171,382, now allowed, filed Jul. 11, 2008.

FIELD OF THE INVENTION

This invention is related to a replacement for strong (low pH) acids in any and all industrial, health, agricultural, mineral, biological, electrical, or other applications. The composition retains the chemical properties of sulfuric acid, but is not immediately harmful to the skin (nondermatropic).

BACKGROUND OF THE INVENTION

Acids are known to have numerous advantageous properties, but their corrosive properties tend to render them unusable in many common situations where the acid cannot be used safely on an industrial level.

Sulfuric acid was first discovered by an Arabic alchemist of the 8$^{th}$ Century CE. It was further refined by later alchemists, and eventually brought to Europe and developed by the alchemist Albertus Magnus. It was originally known as "oil of vitriol", "spirit of vitriol", or often just "vitriol". At one point, it was even considered to be the Philosopher's Stone. Over the centuries, different methods were used to create Sulfuric Acid. In the early 17$^{th}$ Century CE, Johann Glauber employed steam as a medium for carrying off the sulfur from a burning of sulfur and potassium nitrate. The burning potassium nitrate oxidizes the sulfur to $SO_2$ and as a result of mixing with the steam, it yields sulfuric acid.

Although several advancements in manufacturing have been achieved over the centuries, the nature of sulfuric acid has not changed in over 1200 years.

In recent years, however, sulfuric acid has been neutralized to various degrees using a simple process of reversing the addition of the acid to water. Under normal circumstances, one is always cautioned against adding water to acid, due to the resultant reaction. In fact, the following quote on line (www.wikipedia.org) exemplifies the ingrained historical nature of this recommended methodology: "If water is added to the concentrated sulfuric acid, it can react, boil and spit dangerously. One should always add the acid to the water rather than the water to the acid. The necessity for this safety precaution is due to the relative densities of these two liquids. Water is less dense than sulfuric acid, meaning water will tend to float on top of this acid." (Italic emphasis added)

Beginning as early as the 1980s, various chemists and inventors have experimented with the nature of the reaction when the safety precaution listed above is not followed. These experiments have lead to interesting results, some even achieving patented formulations. U.S. Pat. No. 6,565,893 to Jones et al., for example, suspends colloidal metals within a neutralized acid compound for use as a disinfectant for swimming pools. These processes, however, have failed to fully explore and utilize the composition, and also use extremely expensive manufacturing methods to achieve their results. Even the process put forth by Cummins in U.S. Pat. Nos. 5,989,595 and 6,242,011 do not have the same enhanced manufacturing process involved in the production of this product, and therefore do not have the same capacities as a highly protonated, highly charged, highly conductive solution. Instead, they have focused on holding metals in suspension, or at most, using their methods to create a less effective, more expensive, base composition.

Properties of Sulfuric Acid:

60% of total sulfuric acid production is currently used for the wet method of phosphoric acid production, especially as it is consumed in the phosphate fertilizer industry, and as trisodium phosphate for detergents.

Another large consumer of sulfuric acid is the iron/steel-making industries. In this application, it is used to remove rust from raw steel billets before it is delivered to automobile manufacturers. Sulfuric acid is also used for making nylon, in petroleum refining to increase octane, in the manufacture of dyes and pigment solutions, and as an electrolyte in lead batteries. Sulfuric acid can also be used as a drying agent, since it so readily reacts with water.

In fact, the conductivity of sulfuric acid is due to a mechanism akin to the Grotthuss mechanism in water, in which proton switching occurs between the $H_3SO_4^+$ and $HSO_4^-$ ions.

SUMMARY OF THE INVENTION

The present invention is a composition, which is a modified sulfuric acid wherein its corrosive nature is effectively removed and its electrochemical properties are enhanced. As a result of this process, the composition retains its ability to dissolve metals into solution, work as an ultra-low pH compound with germicidal/bactericidal properties, serve as an effective electrolyte, disrupt chemical bonds in organic and inorganic geological deposits, and multiple other functions appropriate for strong acids.

Essentially, the present invention, which is referred to by the inventors herein as the Odysseus 2000 (O2K), is a highly protonated, supercharged, low pH, non-corrosive composition with a milli-volt charge between 400 and 1400, a proton count between $8 \times 10^{24}$ and $14 \times 10^{24}$, and a pH level (at 1 part composition with 99 parts water) between 0.9 and 1.8.

The present invention also comprises a process for making a highly protonated, supercharged, non-corrosive liquid proton suspending composition comprising:

formulating a premixture by mixing a sulfate of between 25% and 45% weight to sulfuric acid of at least 88% purity;

heating said premixture to between 85° and 110° C. and stirring said premixture until the sulfate is completely dissolved;

cooling said premixture to between 65° and 95° C.; and adding water in a controlled manner to said cooled premixture and vigorously stirring and agitating said premixture through the entire process, wherein a weight ratio of premixture to water is between 10:1 and 1:4 and said addition of the water is done in a controlled manner to keep a temperature of an exothermic reaction between 85° and 120° C., and during the addition of the water to said premixture, a DC charge of a predetermined amperage/voltage is rapidly pulsed through the blended water and premixture during the mixing procedure to increase proton count and milli-volt charge, wherein the resultant composition has an electrical charge between 400 and 600 milli-volts (mV), and a proton count of between $8 \times 10^{24}$ and $1.4 \times 10^{25}$; wherein said DC charge of a predetermined amperage/voltage is between 4 and 120 volts and 0.3 to 100 amps.

The first step in the creation of the compound is the heating of highly concentrated sulfuric acid (88% or higher purity) to a temperature near 100° centigrade. To this heated acid we add ammonium sulfate in an amount equal to approximately 10%-25% of the gross weight. The use of crystalline ammonium sulfate can be replaced with other sulfates such as magnesium sulfate, copper sulfate, ammonium bisulfate, sodium sulfate, potassium sulfate, calcium sulfate, aluminum sulfate, or combinations of such sulfates. The heated acid completely dissolves the ammonium sulfate with just a small amount of stirring. Once this has been accomplished, the mixture of acid and sulfate is removed from the heat source and are immediately cooled, in an ice bath or other cooling device such as a jacketed container, or a cryogenic system using liquid nitrogen.

When the temperature has been lowered enough to give a sufficient buffer between the temperature of the mixture (usually about 65° centigrade) and the boiling point of water (100° centigrade), a stirrer is added such as a magnetic or mechanical stirrer, or bubbler inserted, into the mixture. The bubbler should use nitrogen, or liquid nitrogen, as the use of air will cause a reaction that creates water from the oxygen molecules, thus diluting the mixture. It is important that the mixture be kept extremely agitated during the next step of the process.

Also at this time, two electrodes are placed into the mixture. One is connected to a positive wire, the other to a negative wire. The power source (between 4 and 120 volts, 300 mA to 75 A) is turned on and via a strobing pulse interrupter switch; the mixture is pulsed with an electric charge between 10 and 150 times per minute, depending upon the quantity of product, the size of the rods, and the type of power source used.

Water is now added to this mixture in a carefully controlled manner so that the exothermic reaction does not raise the temperature of the new compound over 120° centigrade. The water is added in an open mixing container made of corrosion-resistant materials, with two corrosion-resistant electrodes. The normal amount of water being added is approximately 75%-125% of the acid's gross weight. This is done in 10% increments, whereby the mixture is vigorously stirred and the temperature is carefully monitored. Once the temperature has dropped back down to approximately 80° to 90° centigrade, the next portion of water is added. This is done until the entire quantity of water has been mixed in with the acid/sulfate mixture. The best way to represent this reaction, whereby hydronium ions are created, is:

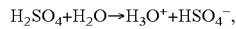

and then

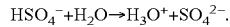

The batch is now left to electrically pulse for a predetermined time such as approximately one hour. This process results in the composition retaining a proton count of between $8 \times 10^{24}$ and $14 \times 10^{24}$, as well as an electrical charge of between 400 and 600 milli-volts.

If the batch is to be supercharged, then the material is left to cool to room temperature (approximately 25° centigrade), and then is put back on the pulsing current for a predetermined time such as approximately one hour. The duration, charge, frequency, amperage and electrode sizes will vary based on batch quantity. The resulting charge is increased to a sustained level of between 800 mV and 1400 mV. This charge is sufficient to electroplate dissolved copper out of the formula and onto stainless steel wool, even if no external charge is applied to the system.

DESCRIPTION OF THE PREFERRED EMBODIMENT

One example of the process to make the invention is as follows:

We began our process with 907 grams of 96% purity sulfuric acid. The acid was heated to approximately 100° centigrade and 207 grams of ammonium sulfate was added. After the ammonium sulfate dissolved completely, the mixture was removed and placed in an ice bath for several minutes, until the temperature had dropped to approximately 65° centigrade.

Once the temperature was sufficiently low, we put two electrodes into the container. In our testing, we used 0.25 inch diameter "316 stainless steel alloy 20" rods as electrodes. These rods were placed in the mix as wide as practicable for the container we used. The rods were then connected to a power source capable of generating 2 amps of current. We have also used as low as 300 mA and as high as 75 amps, depending upon batch size and electrode size. It appears that too much current can "cook" the mixture, raising the temperature beyond the boiling point and rendering the product electrically null. The generator was turned on, with a pulsing strobe circuit interrupter that caused the current to pulse at a rate of approximately 120-130 pulses per minute. At the same time that the pulse is activated, 325 grams of reverse osmosis filtered water was added to the mix in controlled quantities of approximately 32 grams per dose. The addition of the mix creates an exothermic reaction that rapidly raises the temperature in the composition. By limiting the addition, we are able to keep the temperature under 120° centigrade. This temperature was sufficient to create all the necessary chemical reactions, but not so hot that we could not continue adding the water until the entire 325 grams had been mixed.

We then left the system to pulse the new composition for one hour. This resulted in a mV charge of 457 mV, a proton count of $12.1 \times 10^{24}$ and a pH of 1.19 at 1%.

Using a rheostat, we lowered the amperage, and voltage to approximately 75% of its original value. The electricity was then applied in ten minute increments, with readings taken after each ten minute interval until the final charging from 21:55 to 22:05. They were as follows:

| TIME | TEMPERATURE | Milli-VOLTS |
|---|---|---|
| 21:30 | 30° centigrade | 457 |
| 21:40 | 40° centigrade | 1183 |
| 21:52 | 49° centigrade | 1221 |
| 22:05 | 58° centigrade | 1249 |
| 10:00 | 25° centigrade | 1169 |

The final temperature is the milli-volt count as read the following morning, after the composition had been allowed to completely cool to room temperature. It is known that every degree above room temperature (25° centigrade) can give a false reading of the milli-volts by as much as 2% to 5% of the milli-volt count. This charge is known to maintain its level for many weeks.

It should be understood that the preceding is merely a detailed description of one or more embodiments of this invention and that numerous changes to the disclosed embodiments can be made in accordance with the disclosure herein without departing from the spirit and scope of the invention. The preceding description, therefore, is not meant to limit the scope of the invention. Rather, the scope of the invention is to be determined only by the appended claims and their equivalents.

What is claimed is:

1. A process for making a highly protonated, supercharged, non-corrosive liquid proton suspending composition comprising:

formulating a premixture by mixing a sulfate of between 25% and 45% weight to sulfuric acid of at least 88% purity;

heating said premixture to between 85° and 110° C. and stirring said premixture until the sulfate is completely dissolved;

cooling said heated premixture to between 65° and 95° C.; and adding water in a controlled manner to said cooled premixture and vigorously stirring and agitating said premixture through the entire process, wherein a weight ratio of premixture to water is between 10:1 and 1:4 and said addition of the water is done in a controlled manner to keep a temperature of an exothermic reaction between 85° and 120° C., and during the addition of the water to said premixture, a DC charge of a predetermined amperage/voltage is rapidly pulsed through the blended water and premixture during the mixing procedure to increase proton count and milli-volt charge, wherein the resultant composition has an electrical charge between 400 and 600 milli-volts (mV), and a proton count of between $8 \times 10^{24}$ and $1.4 \times 10^{25}$; wherein said DC charge of a predetermined amperage/voltage is between 4 and 120 volts and 0.3 to 100 amps.

2. The process according to claim 1, wherein said sulfate is selected from the group consisting of magnesium sulfate, copper sulfate, ammonium bisulfate, sodium sulfate, potassium sulfate, calcium sulfate, aluminum sulfate, or combinations of such sulfates.

3. The process according to claim 1, further comprising:

continuing to rapidly electrically pulse said premixture for a predetermined time so as to obtain a resultant composition having a charge between of 800 mV and 1400 mV.

* * * * *